(12) United States Patent
Terahara et al.

(10) Patent No.: US 8,691,267 B2
(45) Date of Patent: Apr. 8, 2014

(54) ADHESIVE PATCH

(75) Inventors: Takaaki Terahara, Tsukuba (JP);
Kazunosuke Aida, Tsukuba (JP); Arata Toshimitsu, Tsukuba (JP); Naruhito Higo, Tsukuba (JP)

(73) Assignee: Hisamitsu Pharmaceutical Co., Inc., Tosu-Shi, Saga (JP)

( * ) Notice: Subject to any disclaimer, the term of this patent is extended or adjusted under 35 U.S.C. 154(b) by 1537 days.

(21) Appl. No.: 10/525,646

(22) PCT Filed: Aug. 7, 2003

(86) PCT No.: PCT/JP03/10092
§ 371 (c)(1),
(2), (4) Date: Mar. 24, 2005

(87) PCT Pub. No.: WO2004/019988
PCT Pub. Date: Mar. 11, 2004

(65) Prior Publication Data
US 2005/0260255 A1  Nov. 24, 2005

(30) Foreign Application Priority Data

Aug. 28, 2002 (JP) ................. 2002-249440

(51) Int. Cl.
*A61K 9/70* (2006.01)
*A61F 13/02* (2006.01)

(52) U.S. Cl.
USPC .......................... 424/449; 424/448

(58) Field of Classification Search
USPC ............................... 424/449, 448
See application file for complete search history.

(56) References Cited

U.S. PATENT DOCUMENTS

| 5,656,286 | A | * | 8/1997 | Miranda et al. | 424/449 |
|---|---|---|---|---|---|
| 5,820,876 | A | * | 10/1998 | Hoffmann | 424/449 |
| 5,866,157 | A | * | 2/1999 | Higo et al. | 424/448 |
| 6,461,636 | B1 | * | 10/2002 | Arth et al. | 424/449 |
| 6,495,159 | B2 | * | 12/2002 | Hirano et al. | 424/449 |
| 6,572,879 | B1 | | 6/2003 | Yum et al. | |
| 2004/0028724 | A1 | * | 2/2004 | Terahara et al. | 424/449 |
| 2006/0110433 | A1 | * | 5/2006 | Terahara et al. | 424/448 |

FOREIGN PATENT DOCUMENTS

| EP | 0993 829 A | 4/2000 |
|---|---|---|
| EP | 1 340 496 A1 | 9/2003 |
| JP | 04-266821 A | 9/1992 |
| JP | 04-368323 A | 12/1992 |
| JP | 04-368323 A | 12/1992 |
| JP | 09-301854 A | 11/1997 |
| JP | 09-315957 A | 12/1997 |
| JP | 09-315957 A | 12/1997 |
| JP | 2002-515424 A | 5/2002 |
| WO | WO 96/40139 A | 12/1996 |
| WO | WO 02/38139 A | 5/2002 |

OTHER PUBLICATIONS

The supplementary European search report for EP Application No: 03791200.3; dated Jun. 22, 2011; four pages.

* cited by examiner

*Primary Examiner* — Aradhana Sasan
(74) *Attorney, Agent, or Firm* — Nath, Goldberg & Meyer; Shedlon M. McGee; Tanya E. Harkins

(57) ABSTRACT

A patch comprising a backing layer and an adhesive layer disposed on the backing layer and compounded with a drug and an adhesive base agent, wherein the adhesive base agent comprises styrene-isoprene-styrene block copolymer, 2-ethylhexyl acrylate-vinyl acetate copolymer and a basic nitrogen-including polymer including a basic nitrogen and having no adhesion property at normal temperature.

8 Claims, No Drawings

ADHESIVE PATCH

CROSS-REFERENCED APPLICATIONS

This application is the National Stage of International Application PCT/JP03/10092 filed Aug. 7, 2003, which designated the U.S. and was not published under PCT Article 21(2) in English, and this application claims via the aforesaid International Application the foreign priority benefit of the Japanese Application P2002-249440, filed Aug. 28, 2002, the complete disclosures of said applications are incorporated herein by reference.

TECHNICAL FIELD

The present invention relates to a patch.

BACKGROUND ART

Conventionally, an oral administration method using a tablet, a capsule, a syrup or the like has been known as a method for administering pharmaceutical. However, in recent years, an approach has been tried in which drugs are transdermally administrated using a patch. The administration method using a patch can overcome problems associated with the oral administration method and, in addition, has advantages such as a decrease in the administration frequency, improvement of compliance, ease of administration as well as ease of discontinuation thereof. Therefore, use of a patch is considered promising as a useful administration method for a drug, especially in a case where patients are elderly or children.

However, the stratum corneum of the normal skin has a barrier function for inhibiting exogenous materials from penetrating into the body. Due to the barrier function, compounded medicinal ingredients are often not transdermally absorbed sufficiently when conventional patches are used. Further, since the stratum corneum has a high lipid solubility, the skin permeability of a drug is generally extremely low.

Therefore, in order to enhance the transdermal absorption properties of a drug in the transdermal administration method, studies are being carried out concerning the composition of an adhesive agent for use in a patch and the like. As one part of such studies, a patch has been proposed that uses polymer material such as acrylic polymer or rubber polymer as an adhesive base agent (JP-A-4-266821, JP-A-9-301854 and the like).

DISCLOSURE OF THE INVENTION

However, even when the aforementioned conventional patches are used, the skin permeability of a drug tends to be insufficient. In addition, in these conventional patches, due to a fact that patch properties such as a cohesion property and an adhesion property of the adhesive layer are degraded when a transdermal absorption property of a drug is enhanced, it is very difficult to satisfy all the characteristic features that are required for a patch.

The present invention was achieved in consideration of the problems included in the aforementioned conventional technique, and an object of the invention is to provide a patch that enables a high level to be achieved for both the skin absorption properties of a drug and the patch properties.

The present inventors carried out concentrated studies to achieve the aforementioned object, and found that many of acrylic polymer among polymer materials used in conventional patches have a carboxyl group (—COOH) or a hydroxyl group (—OH) in the molecule as a reaction point for crosslinking, and that it is very difficult to achieve compatibility between the skin permeability of a drug and the patch properties when using this kind of acrylic polymer. As the result of further studies based on this finding, we found that the aforementioned problems could be overcome by forming an adhesive layer of a patch by employing an adhesive base agent containing the following three components: styrene-isoprene-styrene block copolymer, 2-ethylhexyl acrylate—vinyl acetate copolymer, and a basic nitrogen-including polymer including a basic nitrogen and having no adhesion property at normal temperature, to accomplish the invention.

In other words, the patch of the invention is a patch comprising a backing layer and an adhesive layer disposed on the backing layer and compounded with a drug and an adhesive base agent, wherein the adhesive base agent comprises styrene-isoprene-styrene block copolymer, 2-ethylhexyl acrylate—vinyl acetate copolymer and a basic nitrogen-including polymer including a basic nitrogen and having no adhesion property at normal temperature.

According to the invention, by compounding an adhesive base agent containing styrene-isoprene-styrene block copolymer, 2-ethylhexyl acrylate—vinyl acetate copolymer and a basic nitrogen-including polymer including a basic nitrogen and having no adhesion property at normal temperature (hereinafter, simply referred to as "a basic nitrogen-including polymer" depending on the case) in an adhesive layer, the solubility of a drug in the adhesive layer is enhanced sufficiently, and therefore the formation of a formulation can be conducted easily and surely. In addition, since the drug can be compounded in the adhesive layer up to a supersaturated state without crystallization of the drug, the skin permeability of the drug can be enhanced sufficiently.

Furthermore, the aforementioned effects exerted by the patch of the invention become further prominent when a drug with poor water solubility is employed. In other words, in conventional patches, when a drug with poor water solubility is employed, the drug contained in the adhesive layer tends to crystallize to precipitate, thereby leading to a decrease in the skin permeability or a decrease in the adhesion properties with respect to the skin. In contrast, in the patch of this invention, even when a drug with poor water solubility is employed, the solubility of the drug in the adhesive layer is kept at a sufficiently high level, and therefore it is possible to prevent the phenomenon of precipitation of the drug and to achieve a high level for both the skin permeability and the patch properties. As a result, there can be provided a patch for which the transdermal absorbability of a drug is high, which can be stored for a long period of time, and which exerts a sustained pharmacologic effect for a long period of time.

In this connection, the phrase "having no adhesion property at normal temperature" means that, when a polymer is formed into a film shape and a tack test (the rolling ball method, JIS Z 0237) is carried out using the film at ordinary temperature, a ball of any kind does not stop on the film.

In the invention, it is preferable that the basic nitrogen-including polymer is at least one kind selected from methyl methacrylate—butyl methacrylate—dimethyl methacrylate aminoethyl terpolymer and polyvinyl acetal diethylamino acetate.

The patch of the invention is suitable for use in a case where the solubility of a drug to water is 1% or less. When this kind of drug with poor water solubility is used in conventional patches, the skin permeability of the drug or the adhesion properties with respect to the skin become insufficient. In contrast, in the patch of the invention, even when a drug having solubility of 1% or less to water is used, it is possible to obtain a sufficiently high skin permeability and, further, to keep the skin adhesion properties at a high level.

In the patch of the invention, preferably the drug is at least one kind selected from pergolide, pergolide mesylate, nifedipine, nitrendipine and indomethacin.

In the patch of the invention, preferably the adhesive layer further comprises an organic acid.

In the patch of the invention, preferably the adhesive layer further comprises an alicyclic saturated hydrocarbon-based tackifier.

Best Mode for Carrying Out the Invention

Hereinafter, preferable embodiments of the invention will be described in detail.

The patch of the invention is a patch comprising a backing layer and an adhesive layer disposed on the backing layer and compounded with a drug and an adhesive base agent, wherein the adhesive base agent comprises:
(A) styrene-isoprene-styrene block copolymer,
(B) 2-ethylhexyl acrylate—vinyl acetate copolymer, and
(C) a basic nitrogen-including polymer including a basic nitrogen and having no adhesion property at normal temperature.

As the backing layer for use in the patch of the invention, any one may be used without particular limitation insofar as it can support the adhesive layer, and a stretchable or an unstretchable backing layer may be used. Among them, one selected from woven cloth, nonwoven cloth and knitted cloth that have moisture permeability is preferable. Use of a backing layer having moisture permeability allows sweat accumulated between an affected part and the patch upon sticking to effuse effectively and makes it possible to prevent stuffiness and skin stimulation provided by the sweat. As such backing layer, specific examples include cloth and nonwoven cloth, polyurethane, polyester, polypropylene, polyvinyl acetate, polyvinylidene chloride, polyethylene, polyethylene terephthalate and aluminum sheet, one made up to woven cloth, nonwoven cloth or knitted cloth from synthetic or natural fiber such as nylon, acrylic, cotton, rayon or acetate or a complex thereof, and further conjugated material of these and film having moisture permeability and the like. Among them, knitted cloth made of polyester is preferably used from the point of safeness, versatility and stretchability.

Thickness of the backing layer according to the invention is not particularly limited, but a thickness in a range of from 5 to 1000 µm is preferable. A thickness of the backing layer lower than the lowest limit described above tends to decrease operation easiness upon sticking the patch and, on the other hand, that higher than the highest limit described above tends to decrease production easiness in the production process of the patch due to difficulty of cutting the backing layer or the patch, or the like.

In a patch of the invention, an adhesive layer containing a drug and an adhesive base agent is disposed on the backing layer. The adhesive base agent is an adhesive base agent that comprises the polymers (A)-(C) as described above.

(A) The styrene-isoprene-styrene block copolymer is a block copolymer of styrene and isoprene, which has polystyrene at both ends.

The viscosity-average molecular weight of the styrene-isoprene-styrene block copolymer is preferably 30000-2500000, and more preferably 100000-1700000. A viscosity-average molecular weight of the styrene-isoprene-styrene block copolymer that is lower than the lowest limit described above tends to decrease patch properties (especially a cohesion property) and, on the other hand, that higher than the highest limit described above tends to decrease the solubility of the styrene-isoprene-styrene block copolymer with other ingredients in the adhesive layer to make production of a patch difficult.

Examples of this kind of styrene-isoprene-styrene block copolymer include CARIFLEX TR-1101, TR-1107 and TR-1111 (manufactured by Shell Chemical), JSR 5000 and JSR 5002 (trade names, manufactured by JSRR), QUINTAC 3530, 3421 and 3570C (trade names, manufactured by ZEON), Kraton D-KX401CS and D-1107CU (trade names, manufactured by Shell Chemical), Solprene 428 (trade name, manufactured by Philip Petroleum), and the like. One kind of these styrene-isoprene-styrene block copolymers can be used independently or two or more kinds thereof can be used in combination.

The content of the styrene-isoprene-styrene block copolymer in the adhesive base agent is preferably 1-50% by weight, and more preferably 5-25% by weight relative to the total amount of the adhesive base agent. A content of the styrene-isoprene-styrene block copolymer that is lower than the lowest limit described above tends to decrease the skin permeability of the drug and, on the other hand, that higher than the highest limit described above tends to decrease the adhesibility of the patch.

(B) The 2-ethylhexyl acrylate—vinyl acetate copolymer is an acrylic polymer obtained by copolymerizing 2-ethylhexyl acrylate and vinyl acetate, which is substantially free of both carboxyl group and hydroxyl group.

In this connection, when a monomer having a carboxyl group or a hydroxyl group exists in the raw monomer by a small amount as an impurity, or when a side reaction such as thermal degradation occurs upon polymerization in a process for producing the acrylic polymer, a carboxyl group or a hydroxyl group derived from an impurity may be introduced into the acrylic polymer to be obtained. In the present invention, although a carboxyl group or a hydroxyl group derived from interfusion of an impurity or a side reaction such as thermal degradation may be included insofar as a sufficiently high skin permeability of the drug and sufficiently high patch properties belonging to the patch of the invention are not impaired, the use of 2-ethylhexyl acrylate—vinyl acetate copolymer in which carboxyl groups and hydroxyl groups are reduced as far as possible is preferable.

The viscosity-average molecular weight of 2-ethylhexyl acrylate—vinyl acetate copolymer is preferably 200000-1000000. A viscosity-average molecular weight of 2-ethylhexyl acrylate—vinyl acetate copolymer that is lower than the lowest limit described above tends to decrease patch properties (especially an adhesion property) and, on the other hand, that higher than the highest limit described above tends to decrease compatibility with other ingredients contained in the adhesive layer.

Although the content of 2-ethylhexyl acrylate—vinyl acetate copolymer in the adhesive base agent is not particularly limited, it is preferably 1-30% by weight, and more preferably 5-15% by weight relative to the total amount of the adhesive base agent. A content of 2-ethylhexyl acrylate—vinyl acetate copolymer that is lower than the lowest limit described above tends to result in the skin permeability of the drug being insufficient and, on the other hand, that higher than the highest limit described above tends to result in the cohesive force of the adhesion layer being insufficient.

The weight ratio of the content of (A) styrene-isoprene-styrene block copolymer to the content of (B) 2-ethylhexyl acrylate—vinyl acetate copolymer is preferably from 1:9 to 9:1, and more preferably from 1:1 to 9:1. When the weight ratio of the contents (A) and (B) is within the range described above, in particular when a drug with poor water solubility such as pergolide or nifedipine is incorporated in the adhesive layer, the skin permeability of the drug is noticeably enhanced, and a very high level can be achieved for the patch properties. Further, by determining the weight ratio of both contents to a value within the aforementioned range, a moderate adhesibility is provided to the adhesive layer, and sticking properties and skin irritating properties are improved.

Furthermore, the total of the content of (A) styrene-isoprene-styrene block copolymer and the content of (B) 2-ethylhexyl acrylate—vinyl acetate copolymer is preferably 10-50% by weight, and more preferably 10-30% by weight relative to the total amount of the compounds contained in the adhesive layer. When the total of the contents of (A) and (B) is in the aforementioned range, in particular when a drug with poor water solubility such as pergolide or nifedipine is incorporated in the adhesive layer, the skin permeability of the drug is significantly enhanced, and a very high level can be achieved for the patch properties. In addition, by determining the weight ratio of both contents to a value within the aforementioned range, a moderate adhesibility is provided to the adhesive layer, and sticking properties and skin irritating properties are improved.

As (C) a basic nitrogen-including polymer including a basic nitrogen and having no adhesion property at normal temperature, polymers having a functional group such as an amino group, an amide group, an imino group or an imido group may be used. When the basic nitrogen-including polymer has an amino group, the amino group may be any of a primary, a secondary and a tertiary group. Further, when the amino group is either secondary or tertiary, substituted alkyl groups may be linear or form a cycle.

Examples of this kind of basic nitrogen-including polymer include a homopolymer or a copolymer of two or more kinds of polymerizable amines such as dialkylaminoalkyl (meth) acrylate including dimethylaminoethyl (meth)acrylate and diethylaminoethyl (meth)acrylate, and vinyl pyrrolidone, a copolymer of one kind or two or more kinds of the aforementioned polymerizable amines and another polymerizable monomer, and polyvinyl dialkylamino acetate such as polyvinyl acetal diethylamino acetate.

Examples of the monomer capable of polymerizing with polymerizable amine include methyl acrylate, ethyl acrylate, propyl acrylate, butyl acrylate, isobutyl acrylate, hexyl acrylate, octyl acrylate, 2-ethylhexyl acrylate, decyl acrylate, isodecyl acrylate, lauryl acrylate, stearyl acrylate, methyl methacrylate, ethyl methacrylate, butyl methacrylate, isobutyl methacrylate, 2-ethylhexyl methacrylate, decyl methacrylate, isodecyl methacrylate, lauryl methacrylate and stearyl methacrylate.

Among the basic nitrogen-including polymers described above, use of at least one kind selected from methyl methacrylate—butyl methacrylate—dimethylaminoethyl methacrylate terpolymer and polyvinyl acetal diethylamino acetate is preferable because it allows the skin permeability of the drug and the patch properties to be compatible at a higher level. As methyl methacrylate—butyl methacrylate—dimethylaminoethyl methacrylate terpolymer and polyvinyl acetal diethylamino acetate, commercially available Eudragit E (trade name, manufactured by Röhm) and AEA (trade name, manufactured by SANKYO), respectively, and the like can be used.

The viscosity-average molecular weight of the basic nitrogen-including polymer is preferably 100000-5000000, and more preferably 1000000-3000000. A viscosity-average molecular weight of the basic nitrogen-including polymer that is lower than the lowest limit described above tends to decrease patch properties (especially a cohesion property) and, on the other hand, that higher than the highest limit described above tends to decrease compatibility with other ingredients contained in the adhesive layer.

In the adhesive base agent, although the content of the basic nitrogen-including polymer is not particularly limited, it is preferably 1-30% by weight, and more preferably 5-20% by weight relative to the total amount of the adhesive base agent. A content of the basic nitrogen-including polymer that is lower than the lowest limit described above tends to decrease the skin permeability of the drug and, on the other hand, that higher than the highest limit described above tends to decrease adhesive properties of the adhesive layer.

In this connection, in the invention, the adhesive layer may further contain a rubber polymer such as ethylene-vinyl acetate copolymer (EVA, content of vinyl acetate: 5-60% by weight) insofar as the skin permeability of the drug and the patch properties are not impaired. The content of the rubber polymer is preferably 0.05-1% by weight relative to the total amount of the compounds contained in the adhesive layer.

In the patch of the invention, the adhesive layer is compounded with a drug. The drug for use in the invention is not particularly limited, and specific examples thereof include a hypnotic-sedative agent (flurazepam hydrochloride, rilmazafone hydrochloride, phenobarbital, amobarbital and the like), an antipyretic antiinflammatory analgesic (butorphanol tartrate, perisoxal citrate, acetaminophen, mefenamic acid, dichlorophenac sodium, aspirin, alclofenac, ketoprofen, flurbiprofen, naproxen, piroxicam, pentazocine, indomethacin, glycol salicylate, aminopyrine, loxoprofen and the like), a steroid-type antiinflammatory agent (hydrocortisone, prednisolone, dexamethasone, betamethasone and the like), a stimulant antihypnotic agent (methamphetamine hydrochloride, methylphenidate hydrochloride and the like), an agent for psycho neurosis imipramin hydrochloride, diazepam, sertraline hydrochloride, fluvoxamine maleate, paroxetine hydrochloride, citalopram hydrobromide, fluoxetine hydrochloride, alprazolam, haloperidol, clomipramine, amitriptyline, desipramine, amoxapine, maprotiline, mianserin, setiptilline, trazadone, lofepramine, milnacipran, duloxetine, venlafaxine, chlorpromazine hydrochloride, thioridazine, diazepam, meprobamate, etizolam and the like), a hormone drug (estradiol, estriol, progesterone, norethindrone acetate, metenolon acetate, testosterone and the like), a topical anesthetic (lidocaine hydrochloride, procaine hydrochloride, tetracaine hydrochloride, dibucaine hydrochloride, propitocaine hydrochloride and the like), an agent for pollakisuria (oxybutynin hydrochloride, tamsulosin hydrochloride, propiverine hydrochloride and the like), a muscle relaxant suxametonium (tizanidin hydrochloride, eperisone hydrochloride, pridinol mesylate, suxamethonium hydrochloride and the like), an agent for genital organs (ritodrine hydrochloride, meluadrine tartrate), an antiepileptic agent (sodium valproate, clonazepam, carbamazepine and the like), an agent for automatic nerve (carpronium chloride, neostigmine bromide, bethanechol chloride and the like), an antiparkinson agent (pergolide mesylate, bromocriptine mesylate, trihexyphenidyl hydrochloride, amantadine hydrochloride, ropinirole hydrochloride, talipexole hydrochloride, cabergoline, droxidopa, biperiden, selegiline hydrochloride and the like), a hydragogue (hydroflumethiazide, furosemide and the like), a respiratory stimulant (lobeline hydrochloride, dimorpholamine, naloxone hydrochloride and the like), an antimigraine drug(dihydroergotamine mesylate, sumatriptan, ergotamine maleate, flunarizine hydrochloride, cyproheptadine hydrochloride and the like), an antihistamic agent (clemastine fumarate, diphenhydramine tannate, chlorpheniramine maleate, diphenylpyraline hydrochloride, promethazine and the like), a bronchodilator (tulobuterol hydrochloride, procaterol hydrochloride, salbutamol sulfate, clenbuterol hydrochloride, fenoterol hydrobromate, terbutaline sulfate, isoprenaline sulfate, formoterol fumarate and the like), a cardiant (isoprenaline hydrochloride, dopamine hydrochloride and the like), a coronary vasodilator (diltiazem hydrochloride, verapamil hydrochloride, isosorbide dinitrate, nitroglycerine, nicorandil and the like), a peripheral vasodilator(nicametate citrate, tolazoline hydrochloride and the like), a smoking cessation adjuvant (nicotine and the like), an agent for circulation organs (flunarizine hydrochloride, nicardipine hydrochloride, nitrendipine, nisoldipine, felodipine, amlodipine besilate, nifedipine, nilvadipine, manidipine hydrochloride, benidipine hydrochloride, enalapril maleate, delapril hydrochloride, alacepril, imidapril hydrochloride, cilazapril, lisinopril, captopril, trandlapril, perindopril erbumine, atenolol, bisoprolol fumarate, metoprolol tartrate, betaxolol hydrochloride, arotinolol hydrochloride, celiprolol hydrochloride, carvedilol, carteolol hydrochloride, bevantolol hydrochloride, valsartan, candesartan cilexetil, losartan potassium, clonidine hydrochloride and the like), an agent for arrhythmia (propranolol hydrochloride, alprenolol hydrochloride, procainamide hydrochloride, mexiletine hydrochloride, nadolol, disopyramide and the like), an anti-malignant ulcer agent (cyclophosphamide, fluorouracil, tegafur, procarbazine hydrochloride, ranimustine, irinotecan hydrochloride, fluridine and the like), a lipid-lowering agent (pravastatin, simvastatin, bezafibrate, probucol and the like), a hypoglycemic agent (glibenclamide, chlorpropamide, tolbutamide, glymidine sodium salt, glybuzole, and buformin hydrochloride), a therapeutic drug for peptic ulcer (proglumide, cetraxate hydrochloride, spizofurone, cimetidine, and glycopyrronium bromide), a cholagogue (ursodesoxycholic acid, osalmid and the like), an agent for improving the movement of a digestive canal (domperidone, cisapride and the like), an agent for liver disorder (tiopronin and the like), an antiallergic agent (ketotifen fumarate, azelastine hydrochloride and the like), an antiviral agent (acyclovir and the like), a dizziness suppressing agent (betahistine mesylate, difenidol hydrochloride and the like), an antibiotic (cephaloridine, cefdinir, cefpodoximeproxetil, cefaclor, clarithromycin, erythromycin, methylerythromycin, kanamycin sulfate, cycloserine, tetracycline, benzylpenicillin potassium, propicillin potassium, cloxacin sodium, ampicillin sodium, bacampicillin hydrochloride, carbenicillin sodium, chloramphenicol and the like), an agent for habitual addiction (cyanamide and the like), an appetite suppressant (mazindol and the like), a chemotherapeutic agent (isoniazid, ethionamide, pyrazinamide and the like), a blood coagulation accelerator (ticlopidine hydrochloride, and warfarin potassium), an anti-Alzheimer agent (physostigumine, donepezil hydrochloride, tacrine, arecoline, xanomelin and the like), a serotonin-receptor antagonist antiemetic (ondansetron hydrochloride, granisetron hydrochloride, ramosetron hydrochloride, azasetron hydrochloride and the like), an antipodagric (colchicine, probenecid, sulfinpyrazone and the like), a drug-based analgesic (fentanyl citrate, morphine sulfate, morphine hydrochloride, codeine phosphate, cocaine hydrochloride, pethidine hydrochloride and the like) and the like, or pharmaceutically acceptable inorganic or organic salts thereof.

The patch of the invention is very useful in the case where, among the aforementioned drugs, a drug having solubility to water of 1% or less (hereinafter, referred to as "a drug with poor water solubility") such as pergolide mesylate, bromocriptine mesylate, indomethacin, nifedipine, nitrendipine or cabergoline is used, in the respect that a high level can be achieved for both the skin permeability of the drug and the patch properties. In particular, when at least one kind selected from pergolide, pergolide mesylate, nifedipine, nitrendipine and indomethacin is used as the drug, it is possible to achieve compatibility of the aforementioned effects at a high level, which was difficult to achieve with the conventional patches.

Although the compounding amount of the drug according to the invention is suitably selected depending on the kind thereof or the like, it is preferably 0.1-50% by weight relative to the total amount of the compounds contained in the adhesive layer. A compounding amount of the drug that is lower than the lowest limit described above tends to decrease the skin permeability of the drug and, on the other hand, that higher than the highest limit described above tends to decrease physical properties, because the drug may not completely dissolve in the adhesive layer and crystallize to precipitate.

The adhesive layer according to the invention preferably further contains an organic acid in addition to the adhesive base agent and the drug described above. Examples of the organic acid include aliphatic (mono, di, tri) carboxylic acids (acetic acid, propionic acid, citric acid (including anhydrous citric acid), isobutyric acid, caproic acid, caprylic acid, lactic acid, maleic acid, pyruvic acid, oxalic acid, succinic acid, tartaric acid and the like), aromatic carboxylic acids (phthalic acid, salicylic acid, benzoic acid, acetyl salicylic acid and the like), alkyl sulfonic acids (methane sulfonic acid, ethane sulfonic acid, propyl sulfonic acid, butane sulfonic acid, polyoxyethylenealkylether sulfonic acid and the like), alkyl sulfonic acid derivatives (N-2-hydroxyethylpiperidine-N'-2-ethane sulfonic acid), cholic acid derivatives (dehydrocholic acid and the like), and salts thereof (for example, alkali metal salts such as sodium salts), and the like. Among these organic acids, carboxylic acids and salts thereof are preferable, and acetic acid, sodium acetate and citric acid are especially preferable. One kind of these organic acids may be used independently or a mixture of two or more kinds thereof may be used.

In the adhesive layer according to the invention, although the content of the organic acid is not particularly limited, it is preferably 0.01-20% by weight, more preferably 0.1-15% by weight, and further preferably 0.1-10% by weight relative to the total amount of the compounds contained in the adhesive layer. When a content of the organic acid is lower than the lowest limit described above, the effect produced by the organic acid tends to be insufficient with respect to enhancing the skin permeability of the drug and, on the other hand, a content that is higher than the highest limit described above tends to increase skin irritating properties.

In the patch of the invention, the adhesive layer may further comprise an absorption enhancer in addition to the adhesive base agent, the drug, and the organic acid which is compounded according to need. As the absorption enhancer according to the invention, compounds conventionally recognized to have an absorption enhancing effect at the skin may be used, more specifically, the compounds include fatty acids, aliphatic alcohols, fatty acid esters, fatty acid amides, and fatty acid ethers having 6 to 20 carbons, aromatic organic acids, aromatic alcohols, aromatic organic acid esters and ethers, which may be saturated or unsaturated, and also may be linear, branched or cyclic. Further, in the invention, lactic acid esters, acetic acid esters, monoterpenes, sesquiterpenes, Azone, Azone derivatives, glycerin fatty acid esters, propylene glycol fatty acid esters, sorbitan fatty acid esters (Span), polysorbates (Tween), polyethylene glycol fatty acid esters, polyoxyethylene hydrogenated castor oils (HCO), polyoxyethylene alkyl ethers, sucrose fatty acid esters or vegetable oils may be used as an absorption enhancer. Among these absorption enhancers, preferable examples include caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methyl laurate, hexyl laurate, lauric acid diethanol amide, isopropyl myristate, myristyl myristate, octyldodecyl myristate, cehyl palmitate, salicylic acid, methyl salicylate, salicylic acid ethylene glycol, cinnamic acid, methyl cinnamate, cresol, cethyl lactate, lauryl lactate, ethyl acetate, propyl acetate, geraniol, thymol, eugenol, terpineol, L-menthol, borneol, d-limonene, isoeugenol, isoborneol, nerol, dl-camphor, glycerin monocaprirate, glycerin monocaprate, glycerin monolaurate, glycerin monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pirotiodecane and olive oil. Of these, lauryl alcohol, myristyl alcohol, isostearyl alcohol, lauric acid diethanol amide, glycerin monocaprirate, glycerin monocaprate, glycerin monooleate, sorbitan monolaurate, propylene glycol monolaurate, polyoxyethylene lauryl ether and pirotiodecane are more preferable. One kind of these absorption enhancers may be used independently, or two or more kinds thereof may be used in combination.

Although the compounding amount of the absorption enhancer according to the invention is not particularly limited, it is preferably 0.01-20% by weight, more preferably 0.05-10% by weight, and further preferably 0.1-5% by weight relative to the total amount of the compounds contained in the adhesive layer. When a content of the absorption enhancer is lower than the lowest limit described above, the effect produced by the absorption enhancer tends to be insufficient with respect to enhancing the skin permeability of the drug and, on the other hand, a content that is higher than the highest limit described above tends to increase skin irritating properties such as edema.

The adhesive layer according to the invention may further comprise a plasticizer. Specific examples of the plasticizer for use in the invention include petroleum oils (paraffin process oils, naphthene process oils, aromatic process oils and the like), squalane, squalene, vegetable oils (olive oil, camellia oil, castor oil, tall oil, peanut oil), silicone oil, liquid oils (polybutane, liquid isoprene rubber), liquid fatty acid esters (isopropyl myristate, hexyl laurate, diethyl sebacate, diisopropyl sebacate and the like), diethylene glycol, polyethylene glycol, propylene glycol, dipropylene glycol, triacetin, triethyl citrate, crotamiton and the like. Among these plasticizers, liquid paraffin, liquid polybutene, crotamiton, diethyl sebacate and hexyl laurate are especially preferable. One kind of these plasticizers may be used independently or a combination of two or more kinds may be used.

Although the compounding amount of the plasticizer according to the invention is not particularly limited, it is preferably 5-70% by weight, more preferably 10-60% by weight, and further preferably 10-50% by weight relative to the total amount of the compounds contained in the adhesive layer. When the content of the plasticizer is lower than the lower limit described above, the effect produced by compounding the plasticizer tends to be insufficient with respect to enhancing the cohesive force of the patch and, on the other hand, when the content is higher than the highest limit described above the skin permeability of the drug tends to be insufficient.

Specific examples of the tackifier for use in the invention include rosin derivatives (rosin, rosin glycerine ester, hydrogenated rosin, hydrogenated rosin ester, rosin pentaerythritol ester and the like), alicyclic saturated hydrocarbon resin (Arkon P100 (manufactured by Arakawa Chemical Industries) and the like), aliphatic hydrocarbon resin (Quintone B-170 (manufactured by ZEON CORPORATION) and the like), terpene resin (Clearon P-125 (manufactured by Yasuhara Chemical) and the like), maleic acid resin and the like. Among them, hydrogenated rosin glycerine ester, aliphatic hydrocarbon resin and terpene resin are preferable, and alicyclic saturated hydrocarbon resin is especially preferable.

Although the compounding amount of the tackifier according to the invention is not particularly limited, it is preferably 5-70% by weight, more preferably 5-60% by weight, and further preferably 10-50% by weight relative to the total amount of the compounds contained in the adhesive layer. When a compounding amount of the tackifier is lower than the lowest limit described above, the effect produced by compounding the tackifier tends to be insufficient with respect to enhancing the adhesibility of the patch and, on the other hand, a compounding amount higher than the highest limit described above tends to increase skin irritating properties when peeling off the patch.

In the case where an alicyclic saturated hydrocarbon resin is used as a tackifier, it is preferable that the weight ratio of the total content of the polymers (A)-(C) to the content of the tackifier is from 1:3 to 3:1. When the respective contents of the polymers (A)-(C) and the tackifier satisfy the condition described above, both the skin permeability of the drug and the patch properties are enhanced to a greater degree and adhesibility is also enhanced more, whereby a patch can be obtained in which sticking properties and skin irritating properties have been further improved.

Further, in the invention, the adhesive layer may be compounded with an antioxidant, a filler, an ultraviolet absorbent or the like according to need.

Preferable examples of the antioxidant according to the invention include tocopherols and ester derivatives thereof, ascorbic acid, ascorbyl stearate, nordihydroguaiaretic acid, dibutylhydroxytoluene (BHT) and butylhydroxyanisol.

Preferable examples of the filler include calcium carbonate, magnesium carbonate, silicates (such as aluminum silicate and magnesium silicate), silicic acid, barium sulfate, calcium sulfate, calcium zincate, zinc oxide and titanium oxide.

Preferable examples of the ultraviolet absorbent include p-aminobenzoic acid derivatives, anthranilic acid derivatives, salicylic acid derivatives, coumarin derivatives, amino acid-series compounds, imidazoline derivatives, pyrimidine derivatives and dioxane derivatives.

The respective compounding amounts of the aforementioned antioxidant, filler and ultraviolet absorbent are not particularly limited, but the total amount of the antioxidant, the filler and the ultraviolet absorbent is preferably 0-10% by weight, more preferably 0-5% by weight, and further preferably 0-2% by weight relative to the total amount of the compounds contained in the adhesive layer.

There is no particular limitation on a method of disposing the adhesive layer having the aforementioned constitution on the backing layer. For example, the patch of the invention can be obtained by thermally melting a mixture of the adhesive base agent, the drug and other ingredients described above that are added according to need, and then coating the molten mixture on the backing layer. When the patch of the invention further comprises release liner on the adhesive layer, the thermally molten mixture is coated on the release liner followed by laying the backing layer on the coated side, or the thermally molten mixture is coated on the backing layer followed by laying the release liner on the coated side, to obtain the patch of the invention. Furthermore, instead of thermally melting the mixture described above, it is also possible to use a coating liquid prepared by dissolving the mixture in a solvent such as toluene, hexane or ethyl acetate to obtain the patch of the invention.

The patch of the invention may be a patch provided with one adhesive layer, or one provided with two or more adhesive layers insofar as they do not impair the skin permeability of the drug.

Although the thickness of the adhesive layer according to the invention is not particularly limited, it is preferably 20-200 μm. When the thickness of the adhesive layer is lower than the lowest limit described above the skin permeability of the drug tends to be insufficient and, on the other hand, a thickness that exceeds the highest limit described above tends to generate a phenomenon (adhesive agent remaining) in which the adhesive agent remains adhered to the skin after application.

Furthermore, when the patch of the invention comprises release liner, specific examples of the release liner include film made of polyester such as polyethylene terephthalate, polyvinyl chloride, polyvinylidene chloride or the like, and laminate film of bond paper and polyolefin. In these release liners, it is preferable to provide silicone treatment to the side contacting the adhesive layer, because this facilitates ease of operation when peeling the release liner off the adhesive agent.

Hereunder, the invention is explained further specifically on the basis of Examples and Comparative Examples, however the invention is not limited to these examples.

EXAMPLE 1

Pergolide mesylate, sodium acetate and liquid paraffin were charged in a mortar and mixed sufficiently. The mixture was added to a mixed liquid consisting of styrene-isoprene-styrene block copolymer (polymer (A)), 2-ethylhexyl acrylate—vinyl acetate copolymer (polymer (B)), methyl methacrylate—butyl methacrylate—dimethylaminoethyl methacrylate terpolymer (Eudragit E, polymer (C)), an alicyclic saturated hydrocarbon resin and toluene, to prepare a coating liquid for an adhesive layer. The content of the respective ingredients (values relative to the total amount of the compounds excluding toluene), the total content of the polymers (A) and (B), and the weight ratio of the content of the polymer (A) to the content of the polymer (C) in the obtained coating liquid are listed in Table 1.

Next, the obtained coating liquid was applied on a release liner made of polyethylene terephthalate and dried to remove the solvent to form an adhesive layer. Then, a backing layer in the form of knitted cloth made of polyester was laminated to the adhesive layer to obtain the desired patch.

EXAMPLES 2-3, COMPARATIVE EXAMPLES 1-10

In Examples 2-3 and Comparative Examples 1-10, patches were prepared in the same way as Example 1 except that the compositions of the respective coating liquids were determined as listed in Tables 1 and 2.

In this connection, in Comparative Examples 5-10, an acrylic polymer having a carboxyl group (DURO-TA87-2287) or an acrylic polymer having a hydroxyl group (DURO-TA87-2852) (hereinafter, these acrylic polymers are referred to as polymer (D)) was used in place of 2-ethylhexyl-acrylate—vinyl acetate copolymer. In Table 2, the total of polymers (A) and (D), and the weight ratio of (A) and (D) are listed.

(Skin Permeability Test)

The following tests were carried out using the respective patches obtained in Examples 1-3 and Comparative Examples 1-10.

First, dorsal skin of a hairless mouse was extirpated and the skin was set to a flow-through cell, and the periphery of a receptor layer thereof was circulated with water at 37° C., so that the dermis side became a receptor layer side. Next, a patch (application area of the formulation: 5 $cm^2$) was attached to the stratum corneum side of the skin. Normal saline was supplied to the receptor layer, and sampling of the receptor solution was carried out at a speed of 5 mL/hour every 2 hours up to 24 hours. For receptor solutions obtained at the respective times, the flow volume was measured, and drug concentration was measured using high-performance liquid chromatography. From the obtained measurement values, the permeation rate for 1 hour was calculated to obtain a drug permeation rate per unit area of the skin at a steady state. The respective maximum values of the drug permeation rate (maximum skin permeation rate) obtained in the period from the start of the test to 24 hours are listed in Tables 1-2.

(Patch Property Test)

For the respective patches obtained in Examples 1-3 and Comparative Examples 1-10, adhesion properties, cohesion properties and stability of the adhesive layer were evaluated. The evaluation test for the adhesion property was conducted using a probe tack tester and a peel testing machine. The evaluation test for the cohesion property was conducted using a creep measuring machine. The stability was evaluated by conducting the aforementioned adhesion property test for a patch that had been stored at 40° C. for 6 months. Evaluation of these patch properties was conducted on the basis of the following standard:

A: very good
B: good
C: bad.

The obtained results are listed in Tables 1-2.

TABLE 1

| Composition [% by weight] | | | Example 1 | Example 2 | Example 3 | Comparative Example 1 | Comparative Example 2 | Comparative Example 3 | Comparative Example 4 |
|---|---|---|---|---|---|---|---|---|---|
| Composition [% by weight] | (A) | Styrene-isoprene-styrene block copolymer | 12.87 | 10.01 | 7.15 | 14.3 | 21.5 | 16.7 | 7.2 |
| | (B) | 2-Ethylhexyl acrylate-vinyl acetate copolymer | 1.43 | 4.29 | 7.15 | — | 2.4 | 7.2 | 16.7 |
| | (C) | Methyl methacrylate-butyl methacrylate-dimethylaminoethyl methacrylate terpolymer | 9.6 | 9.6 | 9.6 | 9.6 | — | — | — |
| | | Alicyclic hydrocarbon resin | 40.0 | 40.0 | 40.0 | 40.0 | 40.0 | 40.0 | 40.0 |
| | | Liquid paraffin | 15.0 | 15.0 | 15.0 | 15.0 | 15.0 | 15.0 | 15.0 |

TABLE 1-continued

|  |  | Example 1 | Example 2 | Example 3 | Comparative Example 1 | Comparative Example 2 | Comparative Example 3 | Comparative Example 4 |
|---|---|---|---|---|---|---|---|---|
|  | Sodium acetate | 1.8 | 1.8 | 1.8 | 1.8 | 1.8 | 1.8 | 1.8 |
|  | Acetic acid | 5.3 | 5.3 | 5.3 | 5.3 | 5.3 | 5.3 | 5.3 |
|  | Pergolide mesylate | 9.0 | 9.0 | 9.0 | 9.0 | 9.0 | 9.0 | 9.0 |
| Total of (A) and (B) [weight %] |  | 14.3 | 14.3 | 14.3 | 14.3 | 23.9 | 23.9 | 23.9 |
| Weight ratio of (A) to (B) |  | 9:1 | 7:3 | 5:5 | 10:0 | 9:1 | 7:3 | 3:7 |
| Maximum skin permeation rate [$\mu g/cm^2/hr$] |  | 19.6 | 17.0 | 14.8 | 14.0 | 8.6 | 7.0 | 3.6 |
| Patch properties | Adhesion property | B | A | A | C | B | A | B |
|  | Cohesion property | A | A | A | C | B | A | C |
|  | Stability | A | A | A | — | A | A | — |

TABLE 2

|  |  |  | Comparative Example 5 | Comparative Example 6 | Comparative Example 7 | Comparative Example 8 | Comparative Example 9 | Comparative Example 10 |
|---|---|---|---|---|---|---|---|---|
| Composition [% by weight] | (A) | Styrene-isoprene-styrene copolymer | 12.9 | 10.0 | 7.15 | 12.9 | 10.0 | 7.15 |
|  | (B) | 2-Ethylhexyl acrylate-vinyl acetate copolymer | — | — | — | — | — | — |
|  | (C) | Methyl methacrylate-butyl methacrylate-dimethylaminoethyl methacrylate terpolymer | 9.6 | 9.6 | 9.6 | 9.6 | 9.6 | 9.6 |
|  | (D) | DURO-TAK87-2287 | — | — | — | 1.4 | 4.3 | 7.15 |
|  |  | DURO-TAK87-2852 | 1.4 | 4.3 | 7.15 | — | — | — |
|  |  | Alicyclic hydrocarbon resin | 40.0 | 40.0 | 40.0 | 40.0 | 40.0 | 40.0 |
|  |  | Liquid paraffin | 15.0 | 15.0 | 15.0 | 15.0 | 15.0 | 15.0 |
|  |  | Sodium acetate | 1.8 | 1.8 | 1.8 | 1.8 | 1.8 | 1.8 |
|  |  | Acetic acid | 5.3 | 5.3 | 5.3 | 5.3 | 5.3 | 5.3 |
|  |  | Pergolide mesylate | 9.0 | 9.0 | 9.0 | 9.0 | 9.0 | 9.0 |
| Total of (A) and (D) [weight %] |  |  | 14.3 | 14.3 | 14.3 | 14.3 | 14.3 | 14.3 |
| Weight ratio of (A) to (D) |  |  | 9:1 | 7:3 | 5:5 | 9:1 | 7:3 | 5:5 |
| Maximum skin permeation rate [$\mu g/cm^2/hr$] |  |  | 7.0 | 4.4 | 3.0 | 8.6 | 6.8 | 5.0 |
| Patch properties | Adhesion property |  | B | C | C | B | C | C |
|  | Cohesion property |  | C | C | C | C | C | C |
|  | Stability |  | — | — | — | — | — | — |

EXAMPLE 4, COMPARATIVE EXAMPLES 11-13

In Example 4 and Comparative Examples 11-13, patches were prepared in the same way as Example 1 except for using pergolide mesylate as a drug and determining the respective compositions of the coating liquids for the adhesive layer as listed in Table 3.

Next, for the respective obtained patches, the skin permeability of the drug and patch properties were evaluated in the same way as Example 1. The obtained results are listed in Table 3.

EXAMPLE 5, COMPARATIVE EXAMPLES 14-16

In Example 5 and Comparative Examples 14-16, patches were prepared in the same way as Example 1 except for using nifedipine as a drug and determining the respective compositions of the coating liquids for the adhesive layer as listed in Table 3.

Next, for the respective obtained patches, the skin permeability of the drug and patch properties were evaluated in the same way as Example 1. The obtained results are listed in Table 3.

TABLE 3

|  |  |  | Example 4 | Comparative Example 11 | Comparative Example 12 | Comparative Example 13 | Example 5 | Comparative Example 14 | Comparative Example 15 | Comparative Example 16 |
|---|---|---|---|---|---|---|---|---|---|---|
| Composition [% by weight] | (A) | Styrene-isoprene-styrene copolymer | 15.0 | 20.0 | 22.5 | — | 15.0 | 20.0 | 22.5 | — |
|  | (B) | 2-Ethylhexyl acrylate-vinyl acetate copolymer | 15.0 | 20.0 | — | 22.5 | 15.0 | 20.0 | — | 22.5 |
|  | (C) | Methyl methacrylate-butyl methacrylate-dimethylaminoethyl methacrylate terpolymer | 10.0 | — | 17.5 | 17.5 | 10.0 | — | 17.5 | 17.5 |
|  |  | Alicyclic hydrocarbon resin | 40.0 | 40.0 | 40.0 | 40.0 | 40.0 | 40.0 | 40.0 | 40.0 |
|  |  | Liquid paraffin | 15.0 | 15.0 | 15.0 | 15.0 | 15.0 | 15.0 | 15.0 | 15.0 |
|  |  | Pergolide mesylate | 5 | 5 | 5 | 5 | — | — | — | — |
|  |  | Nifedipine | — | — | — | — | 5 | 5 | 5 | 5 |

TABLE 3-continued

|  |  | Example 4 | Comparative Example 11 | Comparative Example 12 | Comparative Example 13 | Example 5 | Comparative Example 14 | Comparative Example 15 | Comparative Example 16 |
|---|---|---|---|---|---|---|---|---|---|
| Total of (A) and (B) [weight %] | | 30.0 | 40.0 | 22.5 | 22.5 | 30.0 | 40.0 | 22.5 | 22.5 |
| Weight ratio of (A) to (B) | | 5:5 | 5:5 | 10:0 | 0:10 | 5:5 | 5:5 | 10:0 | 0:10 |
| Maximum skin permeation rate [µg/cm$^2$/hr] | | 1.5 | 0.3 | 0.7 | 0.5 | 3.2 | 0.2 | 0.8 | 0.3 |
| Patch properties | Adhesion property | A | B | C | C | A | B | C | C |
| | Cohesion property | A | B | C | C | A | B | C | C |
| | Stability | A | — | — | — | A | — | — | — |

EXAMPLE 6, COMPARATIVE EXAMPLES 17-19

In Example 6 and Comparative Examples 17-19, patches were prepared in the same way as Example 1 except for using nitrendipine as a drug and determining the respective compositions of the coating liquids for the adhesive layer as listed in Table 4.

Next, for the respective obtained patches, the skin permeability of the drug and patch properties were evaluated in the same way as Example 1. The obtained results are listed in Table 4.

EXAMPLE 7, COMPARATIVE EXAMPLES 20-22

In Example 7 and Comparative Examples 20-22, patches were prepared in the same way as Example 1 except for using indomethacin as a drug and determining the respective compositions of the coating liquids for the adhesive layer as listed in Table 4.

Next, for the respective obtained patches, the skin permeability of the drug and patch properties were evaluated in the same way as Example 1. The obtained results are listed in Table 4.

The invention claimed is:

1. A patch, comprising:
a backing layer; and
an adhesive layer disposed on the backing layer, the adhesive layer comprising pergolide mesylate and an adhesive base agent comprising
a styrene-isoprene-styrene block copolymer,
2-ethylhexyl acrylate-vinyl acetate copolymer, wherein the weight ratio of the content of the styrene-isoprene-styrene block copolymer to 2-ethylhexyl acrylate-vinyl acetate copolymer is from 1:1 to 9:1, and
a basic nitrogen-containing polymer comprising a basic nitrogen and having no adhesion properties at normal temperature, the basic nitrogen-containing polymer being selected from the group consisting of methyl methacrylate-butyl methacrylate-dimethylaminoethyl methacrylate terpolymer, and polyvinyl acetal diethylamino acetate,
wherein the patch is configured to have a maximum skin permeation rate of 1.5 µg/cm$^2$/hr and to have improved adhesion, cohesion or stability.

2. The patch according to claim 1, wherein the adhesive layer further comprises an alicyclic saturated hydrocarbon-based tackifier.

TABLE 4

|  |  |  | Example 6 | Comparative Example 17 | Comparative Example 18 | Comparative Example 19 | Example 7 | Comparative Example 20 | Comparative Example 21 | Comparative Example 22 |
|---|---|---|---|---|---|---|---|---|---|---|
| Composition [% by weight] | (A) | Styrene-isoprene-styrene copolymer | 15.0 | 20.0 | 22.5 | — | 15.0 | 20.0 | 22.5 | — |
| | (B) | 2-Ethylhexyl acrylate-vinyl acetate copolymer | 15.0 | 20.0 | — | 22.5 | 15.0 | 20.0 | — | 22.5 |
| | (C) | Methyl methacrylate-butyl methacrylate-dimethylaminoethyl methacrylate terpolymer | 10.0 | — | 17.5 | 17.5 | 10.0 | — | 17.5 | 17.5 |
| | | Alicyclic hydrocarbon resin | 40.0 | 40.0 | 40.0 | 40.0 | 40.0 | 40.0 | 40.0 | 40.0 |
| | | Liquid paraffin | 15.0 | 15.0 | 15.0 | 15.0 | 15.0 | 15.0 | 15.0 | 15.0 |
| | | Nitrendipine | 5 | 5 | 5 | 5 | — | — | — | — |
| | | Indomethacin | — | — | — | — | 5 | 5 | 5 | 5 |
| Total of (A) and (B) [weight %] | | | 30.0 | 40.0 | 22.5 | 22.5 | 30.0 | 40.0 | 22.5 | 22.5 |
| Weight ratio of (A) to (B) | | | 5:5 | 5:5 | 10:0 | 0:10 | 5:5 | 5:5 | 10:0 | 0:10 |
| Maximum skin permeation rate [µg/cm$^2$/hr] | | | 1.3 | 0.1 | 0.1 | 0.1 | 5.8 | 1.0 | 1.2 | 0.9 |
| Patch properties | Adhesion property | | A | B | C | C | A | B | C | C |
| | Cohesion property | | A | B | C | C | A | B | C | C |
| | Stability | | A | — | — | — | A | — | — | — |

Industrial Applicability

As described above, according to the patch of the present invention, a high level can be achieved for both the skin absorption property of the drug and the patch properties. Accordingly, the patch of the invention is highly useful when administering a drug transdermally.

3. A patch, comprising:
a backing layer; and
an adhesive layer disposed on the backing layer, the adhesive layer comprising nifedipine and an adhesive base agent comprising
a styrene-isoprene-styrene block copolymer,
2-ethylhexyl acrylate-vinyl acetate copolymer, wherein the weight ratio of the content of the styrene-isoprenestyrene block copolymer to 2-ethylhexyl acrylate-vinyl acetate copolymer is from 1:1 to 9:1, and a basic nitrogen-containing polymer comprising a basic nitrogen and having no adhesion properties at normal temperature, the basic nitrogen-containing polymer being selected from the group consisting of methyl methacrylate-butyl methacrylate-dimethylaminoethyl methacrylate terpolymer, and polyvinyl acetal diethylamino acetate, wherein the patch is configured to have a maximum skin permeation rate of 3.2 μg/cm$^2$/hr and to have improved adhesion, cohesion or stability.

4. The patch according to claim 3, wherein the adhesive layer further comprises an alicyclic saturated hydrocarbon-based tackifier.

5. A patch, comprising:

a backing layer; and an adhesive layer disposed on the backing layer, the adhesive layer comprising nitrendipine and an adhesive base agent comprising a styrene-isoprene-styrene block copolymer, 2-ethylhexyl acrylate-vinyl acetate copolymer, wherein the weight ratio of the content of the styrene-isoprene-styrene block copolymer to 2-ethylhexyl acrylate-vinyl acetate copolymer is from 1:1 to 9:1, and a basic nitrogen-containing polymer comprising a basic nitrogen and having no adhesion properties at normal temperature, the basic nitrogen-containing polymer being selected from the group consisting of methyl methacrylate-butyl methacrylate-dimethylaminoethyl methacrylate terpolymer, and polyvinyl acetal diethylamino acetate, wherein the patch is configured to have a maximum skin permeation rate of 1.3 μg/cm$^2$/hr and to have improved adhesion, cohesion or stability.

6. The patch according to claim 5, wherein the adhesive layer further comprises an alicyclic saturated hydrocarbon-based tackifier.

7. A patch, comprising:

a backing layer; and an adhesive layer disposed on the backing layer, the adhesive layer comprising indomethacin and an adhesive base agent comprising a styrene-isoprene-styrene block copolymer, 2-ethylhexyl acrylate-vinyl acetate copolymer, wherein the weight ratio of the content of the styrene-isoprene-styrene block copolymer to 2-ethylhexyl acrylate-vinyl acetate copolymer is from 1:1 to 9:1, and a basic nitrogen-containing polymer comprising a basic nitrogen and having no adhesion properties at normal temperature, the basic nitrogen-containing polymer being selected from the group consisting of methyl methacrylate-butyl methacrylate-dimethylaminoethyl methacrylate terpolymer, and polyvinyl acetal diethylamino acetate, wherein the patch is configured to have a maximum skin permeation rate of 5.8 μg/cm$^2$/hr and to have improved adhesion, cohesion or stability.

8. The patch according to claim 7, wherein the adhesive layer further comprises an alicyclic saturated hydrocarbon-based tackifier.

* * * * *

UNITED STATES PATENT AND TRADEMARK OFFICE
CERTIFICATE OF CORRECTION

PATENT NO. : 8,691,267 B2  Page 1 of 1
APPLICATION NO. : 10/525646
DATED : April 8, 2014
INVENTOR(S) : Terahara et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1203 days.

Signed and Sealed this
Twenty-ninth Day of September, 2015

Michelle K. Lee
*Director of the United States Patent and Trademark Office*